(12) United States Patent
Welch et al.

(10) Patent No.: US 10,183,945 B2
(45) Date of Patent: Jan. 22, 2019

(54) METHOD OF PREPARING AZA-PYRIDONE COMPOUNDS

(71) Applicant: Alios BioPharma, Inc., South San Francisco, CA (US)

(72) Inventors: Michael Hunter Welch, Mountain View, CA (US); Leonid Beigelman, San Mateo, CA (US); Robert Than Hendricks, San Carlos, CA (US); Andras Horvath, Turnhout (BE); Gareth Brown, Craigavon (GB); Prasad Ganji, Sheffield (GB); Stefan Mix, Craigavon (GB)

(73) Assignee: ALIOS BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 15/455,780

(22) Filed: Mar. 10, 2017

(65) Prior Publication Data

US 2017/0260189 A1 Sep. 14, 2017

Related U.S. Application Data

(60) Provisional application No. 62/306,498, filed on Mar. 10, 2016.

(51) Int. Cl.

| | | |
|---|---|---|
| *C07D 487/04* | (2006.01) | |
| *C07D 301/26* | (2006.01) | |
| *C07F 7/08* | (2006.01) | |
| *C12P 7/22* | (2006.01) | |
| *C07C 29/143* | (2006.01) | |
| *C07C 67/08* | (2006.01) | |
| *C07C 33/46* | (2006.01) | |
| *C07C 45/48* | (2006.01) | |
| *C07F 5/02* | (2006.01) | |

(52) U.S. Cl.
CPC .......... *C07D 487/04* (2013.01); *C07C 29/143* (2013.01); *C07C 33/46* (2013.01); *C07C 45/48* (2013.01); *C07C 67/08* (2013.01); *C07D 301/26* (2013.01); *C07F 5/025* (2013.01); *C07F 7/081* (2013.01); *C07F 7/0829* (2013.01); *C12P 7/22* (2013.01); *C12Y 101/01184* (2013.01); *C12Y 101/9901* (2013.01); *C07B 2200/07* (2013.01)

(58) Field of Classification Search
CPC .................................................. C07D 215/33
See application file for complete search history.

(56) References Cited

U.S. PATENT DOCUMENTS

| | | |
|---|---|---|
| 9,328,119 B2 | 5/2016 | Hendricks et al. |
| 2015/0072982 A1 | 3/2015 | Hendricks et al. |
| 2016/0221963 A1 | 8/2016 | Beigelman et al. |
| 2016/0228438 A1 | 8/2016 | Hendricks et al. |
| 2016/0264581 A1 | 9/2016 | Hendricks et al. |

FOREIGN PATENT DOCUMENTS

| | | |
|---|---|---|
| WO | WO 2015/038660 | 3/2015 |
| WO | WO 2017/223231 | 12/2017 |

OTHER PUBLICATIONS

Alanvert et al., "Highly stereoselective biocatalytic reduction of alpha-halo ketones" Tetrahedron: Asymmetry (2009) 20:2462-2466.
Huang et al., "Oxidation of Sterically Hindered Alcohols to Carbonyls with Dimethyl Sulfoxide-Trifluoroacetic Anhydride" J. Org. Chem. (1976) 41(20):3329-3331.
Montalbetti et al., "Amide bond formation and peptide coupling" Tetrahedron (2005) 61(46):10827-10852.
Carey, Francis, Organic Chemistry, 2nd ed., McGraw Hill, Inc., New York (1992), pp. 328-331.
Gopishetty et. al., "An improved asymmetric synthetic route to a novel triple uptake inhibitor antidepressant (2S,4R,5R)-2-benzhydryl-5-((4-methoxybenzyl)amino)tetrahydro-2H-pyran-4-ol (D-142)" Tetrahedron: Asymmetry (2011) 22(10):1081-1086.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
McMurry, John, Organic Chemistry, 5th ed., Brooks/Cole, Pacific Grove, CA. (2000), Chapter 11.5, pp. 398 and 408.
Streitwieser et al., Introduction to Organic Chemistry, 2nd ed., Macmillan Publishing Co. Inc., New York, NY (1981) pp. 169-171.
International Search Report and Written Opinion of the International Searching Authority dated Jun. 12, 2017 for PCT Application No. PCT/US2017/021800, filed Mar. 10, 2017 nine pages.

*Primary Examiner* — Paul V Ward
(74) *Attorney, Agent, or Firm* — Morrison & Foerster LLP

(57) ABSTRACT

Disclosed herein are methods for obtaining aza-pyridone compounds, which can be useful for ameliorating and/or treating a disease and/or a condition, including an orthomyxovirus infection.

8 Claims, No Drawings

METHOD OF PREPARING AZA-PYRIDONE COMPOUNDS

This application claims priority to U.S. Provisional Patent Application 62/306,498, filed on Mar. 10, 2016, which is incorporated herein it its entirety.

BACKGROUND

Field

The present application relates to the fields of chemistry, biochemistry and medicine. More particularly, disclosed herein are methods for preparing aza-pyridone compounds, which can be useful in treating an orthomyxovirus viral infection.

Description

The viruses of the Orthomyxoviridae family are negative-sense, single-stranded RNA viruses. The Orthomyxoviridae family contains several genera including Influenzavirus A, Influenzavirus B, Influenzavirus C, Isavirus and Thogotovirus. Influenzaviruses can cause respiratory viral infections, including upper and lower respiratory tract viral infections. Respiratory viral infections are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

SUMMARY

Some embodiments disclosed herein relate to a method of preparing compound (I), or a pharmaceutically acceptable salt or solvate thereof. Other embodiments described herein relate to a method of preparing compound (II), or a pharmaceutically acceptable salt thereof.

Some embodiments disclosed herein relate to a method of preparing compound (EE), or a pharmaceutically acceptable salt thereof. Some embodiments disclosed herein relate to a method of preparing compound (A) using compound (A-6), or a pharmaceutically acceptable salt thereof.

Some embodiments disclosed herein relate to compound (CC). Other embodiments disclosed herein relate to compound (DD).

DETAILED DESCRIPTION

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Synthesis

The compounds described herein may be prepared in various ways. General synthetic routes, and some examples of starting materials used to synthesize the compounds shown are described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Some embodiments described herein relate to a method of preparing compound (I), or a pharmaceutically acceptable salt or solvate thereof, that can include the use of compound (C), wherein compound (I) and compound (C) can have the following structures:

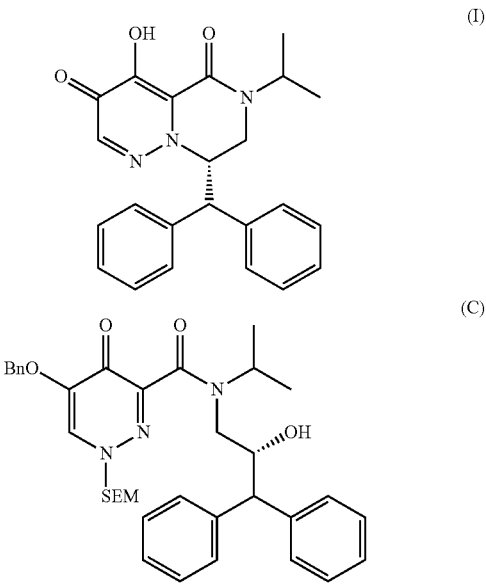

wherein compound (C) can be obtained from the coupling of compound (A) with compound (B) using 1,1'-carbonyldiimidazole (CDI), wherein compound (A) and compound (B) can have the following structures:

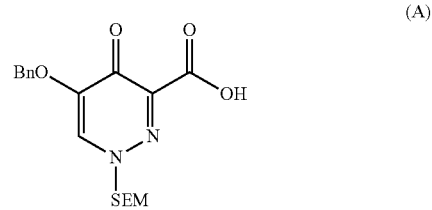

(B)

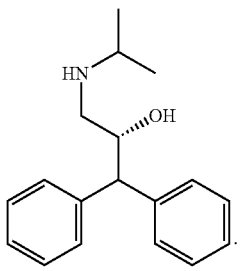

In embodiments, compound (A) and compound (B) are coupled in the presence of CDI or O-(7-azabenzotriazol-1-yl)-N,N,N',N'-tetramethyluronium hexafluorophosphate (HATU). Coupling compound (A) and compound (B) in the presence of CDI provided a higher yield of compound (C). The coupling reaction between compound (A) and compound (B) can be conducted in a variety of solvent(s). In some embodiments, the solvent can be toluene. In some embodiments, a base can also be present during the reaction between compound (A) and compound (B). Suitable bases include, but are not limited to, an optionally substituted amine base, such as an alkylamine (including mono-, di- and tri-alkylamines (for example, monoethylamine, diethylamine, trimethylamine, and N,N-Diisopropylethylamine (DIEA)), optionally substituted pyridines (such as collidine) and optionally substituted imidazoles (for example, N-methylimidazole)).

The temperature and time of the coupling reaction can vary. In some embodiments, the reaction between compound (A) and compound (B) can take place at an elevated temperature, for example, above room temperature (~25° C.). In some embodiments, the reaction between compound (A) and compound (B) can take place at a temperature in the range of about 45° C. to about 65° C. In some embodiments, the reaction between compound (A) and compound (B) can take place at a temperature in the range of about 50° C. to about 60° C. In some embodiments, the time of the reaction between compound (A) and compound (B) can be in the range of about 1 hour to about 8 hours. In some embodiments, the time of the reaction between compound (A) and compound (B) can be in the range of about 3 hours to about 5 hours.

In some embodiments, a method described herein can include transforming the hydroxy group of compound (C) to $LG^1$, wherein $LG^1$ can be a leaving group, to form compound (D), wherein compound (D) can have the following structure:

(D)

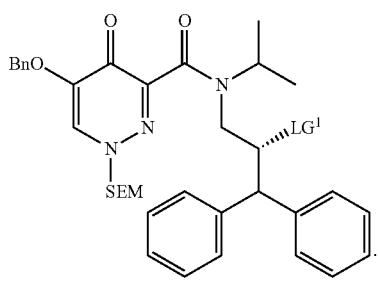

An example of a suitable leaving group ($LG^1$) can be an electrophilic activating group, such as —OC(=O)CF$_3$. The leaving group, —OC(=O)CF$_3$, can be formed from trifluoroacetic anhydride (TFAA). The formation of compound (C) can be conducted in a variety of solvent(s). In some embodiments, the solvent can be toluene. In some embodiments, this reaction to form compound (D) can take place at a temperature in the range of about 20° C. to about 35° C. In some embodiments, this reaction to form compound (D) can take place at a temperature in the range of about 25° C. to about 30° C. In some embodiments, the time of the reaction to form compound (D) can be in the range of about 6 hours to about 14 hours. In some embodiments, the time of the reaction between compound (A) and compound (B) can be in the range of about 9 hours to about 11 hours.

In some embodiments, a method described herein can include removing the 2-(trimethylsilyl)ethoxy]methyl (SEM) group from compound (D) using a reagent selected from an acid and a fluoride source to form compound (E), wherein compound (E) can have the following structure:

(E)

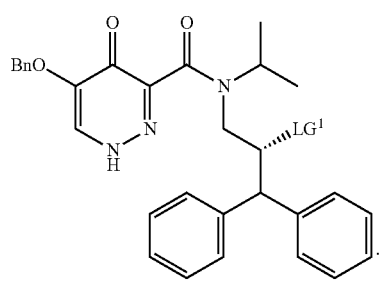

Examples of suitable regents that can remove the SEM group include, but are not limited to, HCl in 1,4-dioxane, trifluoroacetic acid, triethylamine·3HF (TEA·3HF), pyridine-HF, Bu$_4$NF (TBAF), cesium fluoride, lithium tetrafluoroborate or a combination of one or more of the aforementioned. The formation of compound (E) can be conducted in various solvent(s). In some embodiments, the solvent can be toluene.

In some embodiments, a method described herein can include removing the benzyl (Bn) group from compound (E) to form compound (F), wherein compound (F) can have the following structure:

(F)

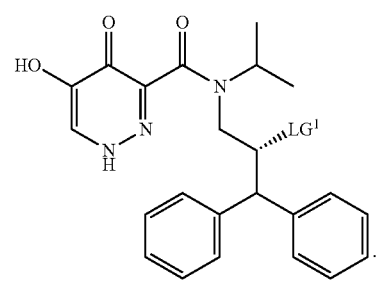

The benzyl group can be removed by a variety of agent(s), such as, one or more selected from Pd/C, Pd(OH)$_2$/C, PtO$_2$, H$_2$, formic acid, TMSI, DCM, BF$_3$-OEt$_2$, NaI, CH$_3$CN, Ac$_2$O H$_2$SO$_4$, FeCl$_3$, Et$_3$SiH and bis(trimethylsilyl)acetamide (BSA). In some embodiments, the benzyl group can be removed via hydrogenolysis using a Pd or Pt catalyst, such as those described herein, and a hydrogen source, for example H$_2$ or formic acid. In some embodiments, the benzyl group of compound (E) can be removed using Pd/C, H$_2$ and BSA. BSA assisted in maintaining the reactants in solution decreasing the formation of polymeric byproducts. The removal of the benzyl group from compound (E) to form compound (F) can be conducted in a suitable solvent(s). In some embodiments, the solvent can be toluene.

In some embodiments, a method described herein can include forming compound (I) via a cyclization reaction of compound (F). The moiety, LG$^1$, can be displaced and compound (I) can be formed via cyclization. The cyclization of compound (F) to form compound (I) can be conducted under various condition(s) and various solvent(s). In some embodiments, cyclization can be conducted using an amine base. Examples of suitable amine bases are described herein. In some embodiments, the amine base can be DIEA. In some embodiments, the solvent can be toluene.

The temperature and time of the cyclization reaction of compound (F) can vary. In some embodiments, the cyclization reaction can take place at an elevated temperature. In some embodiments, the cyclization of compound (F) can take place at a temperature in the range of about 80° C. to about 130° C. In some embodiments, the cyclization of compound (F) can take place at a temperature in the range of about 90° C. to about 120° C. In some embodiments, the time of the cyclization reaction can be in the range of about 0.5 hour to about 3.5 hours. In some embodiments, the time of cyclization reaction of compound (F) can be in the range of about 1 hour to about 3 hours.

In some embodiments, a method described herein can include recrystallizing compound (I) and obtaining compound (I) as a solvate. In some embodiments, the recrystallization can be conducted using isopropyl alcohol and obtaining compound (I) as an isopropyl alcohol solvate.

In some embodiments, a method described herein can include adding a —C(═O)CH(CH$_3$)$_2$ group to the hydroxy group attached to the fused bicyclic ring of compound (I) to form compound (II), wherein compound (II) can have the following structure:

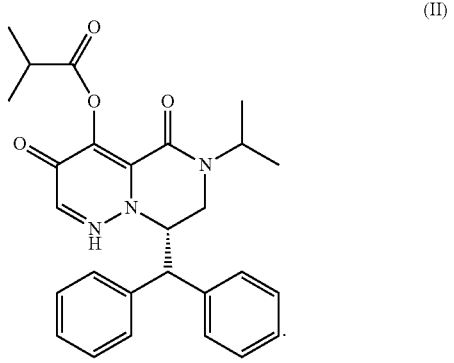 [SMILES: CC(C)C(=O)Oc1c2n(ncc1=O)[C@@H](C(c1ccccc1)c1ccccc1)CN(C(C)C)C2=O]

(II)

In some embodiments, the —C(═O)CH(CH$_3$)$_2$ group can be added using LG$^2$C(═O)CH(CH$_3$)$_2$, wherein LG$^2$ can be a suitable leaving group. In some embodiments, LG$^2$ can be Cl (chloro). The temperature and time for forming compound (II) can vary. In some embodiments, the formation of compound (II) can take place at approximately room temperature. In some embodiments, the cyclization of compound (F) can take place at a temperature in the range of about 20° C. to about 25° C. In some embodiments, the time of the cyclization reaction can be in the range of about 1 hour to about 6 hours. In some embodiments, the time of cyclization reaction of compound (F) can be in the range of about 2 hours to about 4 hours.

In some embodiments, compound (II) can be obtained by crystallizing the compound out of a solvent solution. In some embodiments, compound (II) can crystallize out of a solution that includes an ester and a hydrocarbon. For example, compound (II) can crystallize from EtOAC and/or iPrOAC in combination with n-heptane. In some embodiments, the formation of compound (I), or a pharmaceutically acceptable salt or solvate thereof, and/or compound (II), or a pharmaceutically acceptable salt thereof, from compound (A) and Compound (B) can be conducted on a multi-kilogram scale.

Some embodiments described herein relate to a method of preparing a compound (EE) that can include the use of compound (DD), wherein compound (DD) and compound (EE) can have the following structures:

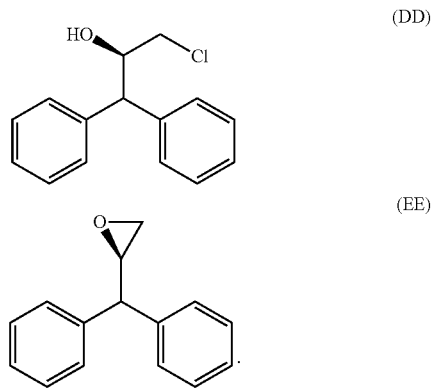

Compound (EE) can be formed using a base. Examples of suitable bases include, but are not limited to, potassium carbonate, sodium carbonate, sodium bicarbonate, potassium bicarbonate, calcium carbonate cesium carbonate, potassium hydroxide and combinations thereof.

In some embodiments, a method described herein can include ring opening compound (EE) to obtain compound (B), wherein the structure of compound (B) is shown herein. In some embodiments, the ring opening can be conducted using H$_2$N—CH(CH$_3$)$_2$ to form the amino alcohol, compound (B). In some embodiments, compound (B) can be obtained as a salt, for example, a hydrochloride salt.

In some embodiments, a method described herein can include obtaining compound (DD) by asymmetrically reducing compound (CC), wherein compound (CC) can have the following structure:

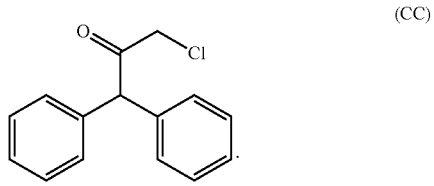 [SMILES: O=C(CCl)C(c1ccccc1)c1ccccc1]

(CC)

In some embodiments, compound (DD) can be obtained using a borane reagent and a boron-based catalyst. Various borane reagents can be used. A non-limiting list of suitable borane reagents include BH$_3$-THF, BH$_3$-Me$_2$S (BMS), BH$_3$-Et$_2$NPH and BH-catechol. A variety of boron-based catalysts can also be utilized. In some embodiments, the boron-based catalyst can be selected from

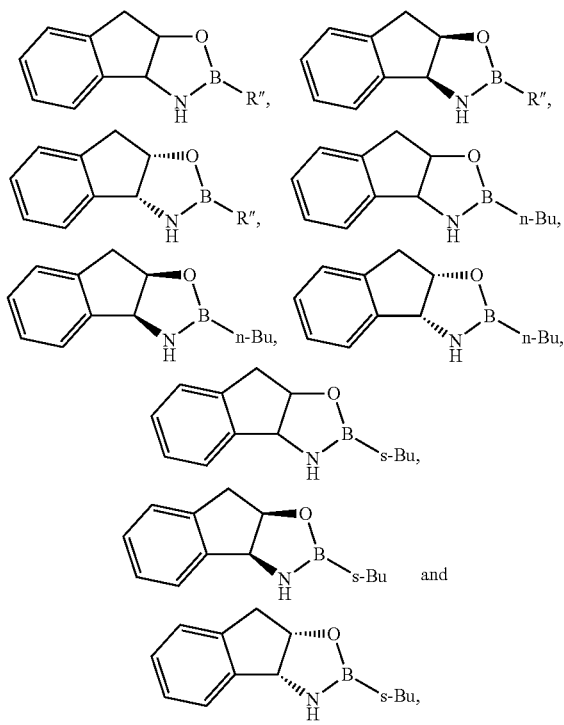

wherein R" can be an unsubstituted $C_{1-4}$ alkyl or an optionally substituted phenyl.

The reaction to form compound (DD) can be conducted in a variety of solvent(s). In some embodiments, the solvent can be a polar aprotic solvent. Examples of polar aprotic solvents are describe herein, but are not limited to, dimethylformamide, tetrahydrofuran, ethyl acetate, acetone, acetonitrile, dimethyl sulfoxide or methyl isobutyl ketone. In some embodiments, the solvent can be tetrahydrofuran (THF). The time and temperature of the asymmetric reduction to form compound (DD) can vary. In some embodiments, the temperature can be in the range of about 15° C. to about 50° C. In some embodiments, the time of the asymmetric reduction to form compound (DD) can be in the range of about 0.5 hour to about 2.5 hours. In some embodiments, the time of the asymmetric reduction to form compound (DD) can be about 1.5 hours.

In alternative embodiments, compound (DD) can be obtained by asymmetrically reducing compound (CC) with the use of a carbonyl reductase, thereby allowing for high enantiomeric selectivity. Commercially available kits containing different ketoreductases or carbonyl reductases are available from multiple vendors. For example, a compound of Formula (CC) may be incubated with the ketoreductase or carbonyl reductase to be screened in the presence of a hydride source. In one embodiment of the invention, the ketoreductase or carbonyl reductase is selected from any one or ALMAC Carbonyl Reductases CRED-121, CRED-41, CRED-52, CRED-155, and CRED-163 (each commercially available from ALMAC Group Ltd., Craigavon, England). In certain preferred embodiments, the enzyme is selected from CRED-121 and CRED-41. In more preferred embodiments, the enzyme is CRED-121.

In such alternative embodiments, the process of this invention involves the presence of a hydride source. The term "hydride source" refers to a compound or mixture that is capable of providing a hydride anion or a synthetic equivalent of a hydride anion. A co-factor used with the ketone reductase or carbonyl reductase in the process of this invention can be selected from those known in the art. In some embodiments, the cofactor is selected from NAD and NADP. The choice of co-factor may be based upon (a) the presence or absence of a co-factor regeneration system; (b) the requirement for a hydride source; and (c) compatibility with the specific ketone reductase or carbonyl reductase employed. Selection of a co-factor may be guided by information from the commercial supplier of the specific ketone reductase or carbonyl reductase.

In another embodiment, the hydride source additionally comprises a co-factor regeneration system. The high cost of co-factors can make their use on a stoichiometric basis impractical. A low-cost co-factor regeneration system continually produces and regenerates the reduced form of the co-factor, requiring the co-factor to be present in only catalytic amounts. Moreover, the use of a co-factor regeneration system eliminates the need to use a reduced co-factor or a deuterated co-factor. The co-factor regeneration system produces the required reduced or reduced and deuterated co-factor in situ. Accordingly, any cofactor or combinations of cofactors compatible with the chosen ketone reductase or carbonyl reductase can be employed with a co-factor regeneration system. In this embodiment, NAD is interchangeable with NADH and $NAD^2H$; and NADP is interchangeable with NADPH and $NADP^2H$. Similarly, the designations "—NAD" and "—NADH", and "—NADP" and "—NADPH", respectively, are used interchangeably herein in conjunction with enzymes that use, respectively, NADH and NADPH as co-factors.

A typical co-factor regeneration system consists of a dehydrogenase and a substrate for that dehydrogenase. Upon catalysis by the dehydrogenase, its substrate provides a hydride anion to regenerate (reduce) the cofactor. The newly reduced cofactor can then subsequently donate a hydride or deuteride atom to the compound of Formula (CC) to provide a compound of Formula (DD). Examples of hydride cofactor regeneration systems useful in the present invention include, but are not limited to, reducing sugars and their corresponding hydrogenase, such as glucose and glucose dehydrogenase ("GDH").

In some embodiments, a method described herein can include converting compound (BB) to compound (CC) using a chloride source, wherein compound (BB) can have the following structure:

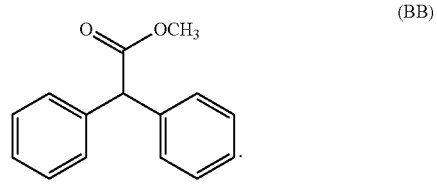 [SMILES: COC(=O)C(c1ccccc1)c1ccccc1]

(BB)

A variety of chloride sources can be used. In some embodiments, the chloride source can be $ClCH_2COONa$. Alternatively, converting compound (BB) to compound (CC) can be conducted using $X^1CH_2COONa$, wherein $X^1$ can be a halide or pseudohalide. Examples of pseudohalides include, but are not limited to CN, OCN, SCN, $N_3$, and a triflate. In some embodiments, forming compound (CC) can include using an amine base. A variety of suitable amine bases are described herein. In some embodiments, the amine base can be trimethylamine. The formation of compound (CC) can be conducted in various of solvent(s). In some embodiments, the solvent can be a polar aprotic solvent, such as those described herein. In some embodiments, the solvent can be tetrahydrofuran (THF). The time and temperature for forming compound (CC) can vary. In some embodiments, the temperature can be in the range of about −25° C. to about 35° C. In some embodiments, the time of the asymmetric reduction to form compound (DD) can be in the range of about 0.5 hour to about 2 hours. In some embodiments, the time of the asymmetric reduction to form compound (DD) can be about 1 hour.

In some embodiments, a method described herein can include esterifying compound (AA) to obtain compound (BB), wherein compound (AA) can have the following structure:

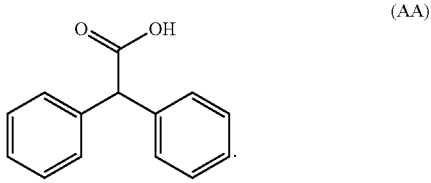 [SMILES: O=C(O)C(c1ccccc1)c1ccccc1]

(AA)

Various methods for esterifying compound (AA) are known to those skilled in the art. In some embodiments, compound (BB) can be obtained via Fischer esterification conditions using an alcohol and an acid catalyst. In some embodiments, the alcohol can be MeOH, and the acid catalyst can be $H_2SO_4$.

Some embodiments described herein relate to a method of preparing compound (A) from compound (A-6)

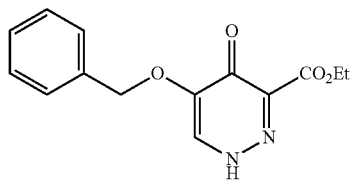

A-6 that can include adding a SEM group and converting —$CO_2Et$ group to —COOH. Compound (A) prepared from compound (A-6) can be used to prepare compound (I) and/or compound (II) as described herein.

There are several advantages of using one or more methods described herein. As shown herein, the formation of compound (I) from compound (A) and compound (B) can be conducted utilizing a single solvent (for example, toluene). As a result, it may be unnecessary to isolate one or more of compound (C), compound (D), compound (E) and/or compound (F) when obtaining compound (I) from compound (A) and compound (B). In some embodiments, a method described herein can result reduced loss of product(s) in one or more reactions (for example, forming an increased amount of compound (C) compared to an existing method), reduction in the amount of one or more byproducts formed and/or fewer purification steps compared to an existing method.

An advantage of the disclosed methods includes obtaining compound (EE) without losing at least half of the starting material in the synthesis of compound (B). As shown herein, compound (DD) is a single enantiomer, and thus, compound (EE) can be obtained from compound (DD) with a yield of greater than 50%. By comparison, existing methods (such as those described in Gopishetty et. al., *Tetrahedron: Asymmetry* (2011) 22(10):1081-1086 using Jacobsen's catalyst) result in at least half of the staring material being lost to the diol (see compound 8 in Scheme 1 of Gopishetty et. al.). Thus, the yield of compound (EE) from an existing method cannot be greater than 50%. In addition, forming compound (DD) via an asymmetric reduction as described herein compared to existing methods, can be that the asymmetric reduction reaction described herein is more stable compared to the Jacobsen's resolution described in existing methods.

EXAMPLES

Additional embodiments are disclosed in further detail in the following examples, which are not in any way intended to limit the scope of the claims.

Example 1—Compound (A)

Route 1

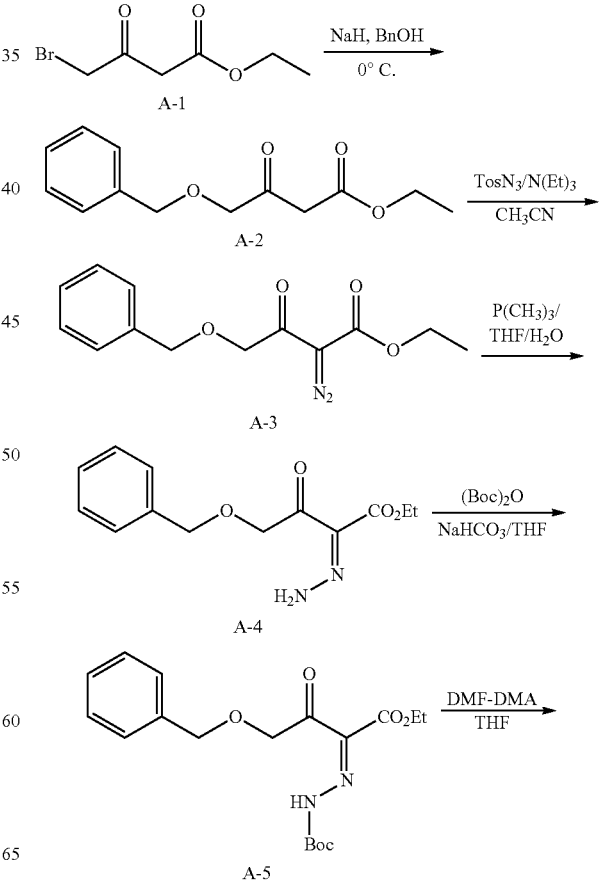

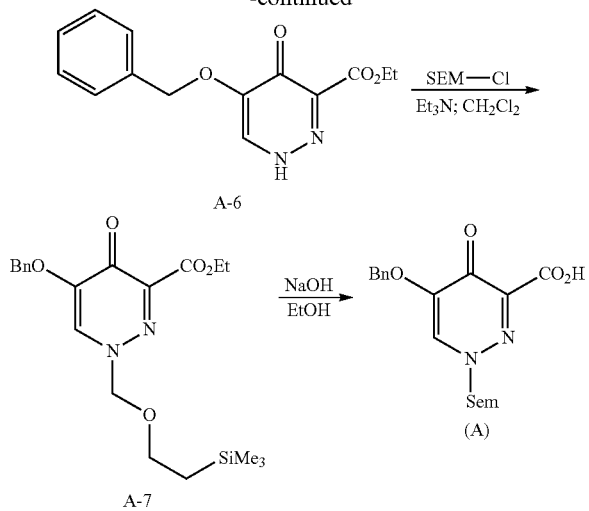

To a stirred solution of NaH (21.8 g, 912 mmol 3.0 eq.) in THF (300 mL) was added BnOH (32.8 g, 304.0 mmol 1.0 eq.) under a $N_2$ atmosphere at 0° C. After addition, the mixture was stirred for 30 mins. Compound A-1 (63.5 g, 304.0 mmol 1.0 eq.) was added portionwise. The mixture was allowed to warm to ambient temperature and stirred for another 12 h. The reaction was monitored by TLC (petroleum ether (PE):EtOAc=5:1). The mixture was poured into 2M HCl solution to a ~pH 6. The solution was extracted with EtOAc (200 mL×3). The combined organic phases were dried over $Na_2SO_4$, filtered and concentrated. The residue was purified by column chromatography on silica gel (PE:EtOAc=30:1 to 5:1) to give A-2 as a colorless oil (46 g, 88.5%). $^1$H NMR (CDCl$_3$) δ 7.39-7.29 (m, 5H), 4.59 (s, 2H), 4.17-4.24 (q, 2H), 4.14 (s, 2H), 3.53 (s, 2H), 1.31-1.22 (t, 3H).

To a stirred solution of A-2 (10.0 g, 42.3 mmol 1.0 eq.) in $CH_3CN$ (20 mL) under a $N_2$ atmosphere at 0° C., was added TosN$_3$ (8.35 g, 42.3 mmol 1.0 eq.) and TEA (12.84 g, 127.1 mmol 3.0 eq.). The mixture was stirred at 0° C. for 2 h. The mixture was warmed to room temperature (RT) and stirred for 6 h. The reaction was monitored by TLC (PE:EtOAc=5:1). After complete conversion was observed, the solvent was removed under reduced pressure, and the residue was purified by column chromatography on silica gel (PE:EtOAc=30:1 to 5:1) to give A-3 as a colorless oil (4.5 g, 40.5%). $^1$H NMR (CDCl$_3$) δ 7.39-7.26 (m, 5H), 4.64 (s, 2H), 4.60 (s, 2H), 4.29-4.24 (q, 2H), 1.32-1.28 (t, 3H).

To a solution of A-3 (4.04 g, 15.4 mmol 1.0 eq.) in THF (5 mL) was added $P(CH_3)_3$/THF solution (16.9 mL, 16.9 mM, 1.1 eq.) at RT. The mixture was stirred for 15 mins (indicated by TLC, PE:EtOAc=2:1) and then quenched with water (2.8 mL). The mixture was stirred for 15 mins and concentrated under reduced pressure. The crude residue was purified by column chromatography on silica gel (PE:EtOAc=5:1 to 2:1) to give A-4 as a yellow solid (4.0 g, 98.2%). $^1$H NMR (CDCl$_3$) δ 7.39-7.24 (m, 5H), 4.66-4.66 (s, 1H), 4.66-4.61 (s, 2H), 4.53-4.53 (s, 1H), 4.31-4.24 (m, 2H), 1.35-1.29 (m, 3H).

To a stirred solution of A-4 (20.0 g, 75.7 mmol, 1.0 eq.) in THF (100 mL) was added NaHCO$_3$ (19.1 g, 227.3 mmol 3.0 eq.) and (Boc)$_2$O (22.84 g, 113.6 mmol 1.5 eq.). The mixture was heated to reflux for 6 h and monitored by TLC (PE:EtOAc=2:1). After complete conversion was observed, the solution was concentrated under reduced pressure. The residue was dissolved in EtOAc (200 mL) and washed with water (80 mL×2). The organic layer was separated, dried over Na$_2$SO$_4$ and filtered. The mixture was concentrated under reduced pressure, and the residue was purified by column chromatography on silica gel (PE:EtOAc=8:1) to give A-5 as a white solid (15 g, 54.30%). $^1$H NMR (CDCl$_3$) δ 11.59 (s, 1H), 7.40-7.26 (m, 5H), 4.71-4.61 (m, 2H), 4.39 (s, 2H), 4.71-4.27 (q, 2H), 1.70-1.48 (m, 9H), 1.38-1.24 (t, 3H).

To a solution of A-5 (4.2 g, 11.5 mmol 1 eq.) in THF (100 mL) at RT, was added DMF-DMA (6.15 g, 51.7 mmol, 4.5 eq.). The mixture was stirred at RT for 16 h. After complete conversion was observed as indicated by TLC, the reaction was treated with water (5~6 mL) and stirred for 30 mins. The solvent was evaporated under reduced pressure at 40-50° C. The residue was crystallized from EtOAc to give the pure product as a white solid, (0.5 g). The mother liquor was concentrated and purified by column chromatography on silica gel (DCM:MeOH=50:1 to 10:1) to give A-6 as a solid (2.4 g, total 75.95%). LCMS (ESI) m/z=275.2 [M+H]$^+$ (calc.=274.1). Retention Time=1.097 min.

To a solution of A-6 (2.74 g, 10 mmol) and TEA (3.03 g, 30 mmol) in DCM (40 mL) at 0° C., was added 2-trimethylsilylethoxymethyl chloride (SEMCl, 2.86 g 0.20 mmol) dropwise. After addition, the mixture was stirred at 0° C. for 1 h. The solution was then slowly warmed to RT and stirred for 2 h. The reaction was quenched, washed with 1 M HCl aqueous solution (30 mL×3), sat. aq. NaHCO$_3$ (20 mL×2) and water. The organic layer was washed with brine, dried over Na$_2$SO$_4$, and concentrated to give a crude oil (3.8 g), which was then purified by column chromatography on silica gel to give A-7 as a colorless oil (3.0 g, 74%).

To a stirred solution of A-7 (2.02 g, 5.0 mmol) in MeOH (20 mL) at 0° C., was added aq. NaOH (1 M, 5 mL) dropwise. After addition, the mixture was stirred for 30 mins. MeOH was removed under reduced pressure. The resulting aqueous solution was neutralized with 1 M HCl to pH ~2.0. A white solid precipitated, which was then filtered, washed with water and dried in vacuum to get compound (A) (1.5 g, 83%) with a high purity. $^1$H NMR (400 MHz, DMSO-d 6): δ 8.88 (s, 1 H), 7.49-7.41 (m, 5 H), 5.57 (s, 2 H), 522 (s, 2 H), 3.63 (t, J=8 Hz, 2H), 0.87 (t, J=8 Hz, 2H), 0.02 (S, 9 H).

Example 2—Compound (A)

Route 2

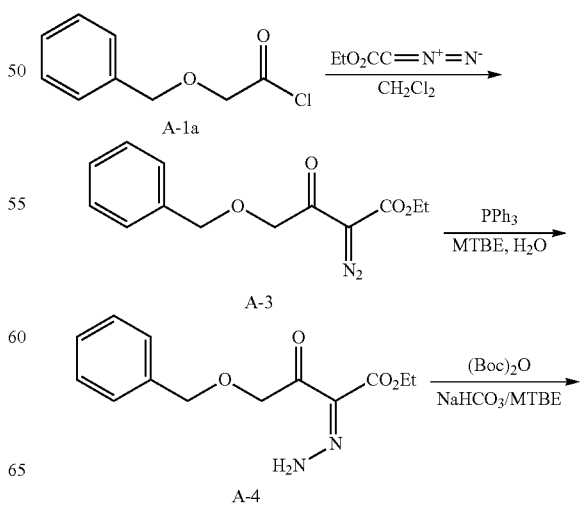

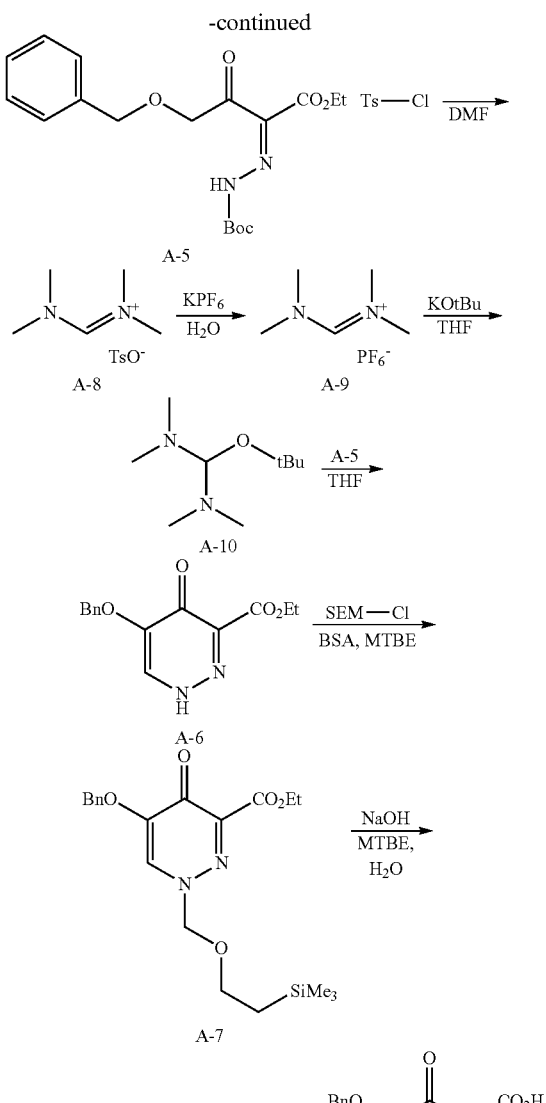

To a stirred solution of A-1a (85.0 g, 460 mmol, 1.0 eq.) in CH$_2$Cl$_2$ (170 mL) under a N$_2$ atmosphere cooled to below 18° C., was added, dropwise, a solution of ethyl diazoacetate (116.7 g, 1023 mmol, 2.2 eq.) in CH$_2$Cl$_2$ (680 mL). The rate of addition and external cooling was controlled to maintain the reaction temperature below 20° C. At the end of the addition the reaction was stirred at 25-30° C. for 40 h. The mixture was cooled to 10-15° C. and treated with 20 wt % K$_2$CO$_3$ (aq.) solution (340 mL). The organic layer was separated, washed with brine (425 mL), and separated. Vacuum solvent exchange using MTBE (3×850 mL) was performed (bath temperature was maintained below 35° C.), resulting in an MTBE solution of A-3 (~1275 mL) that can be used directly in the next step without further purification.

To an MTBE solution of A-3 (~735 mL) was added PPh$_3$ (80.0 g, 305 mmol, 1.15 eq.) at 20-25° C. The reaction was stirred for 1 h (indicated by TLC, PE:EtOAc=2:1), treated with water (62 mL), and stirred for 10 h at 50-60° C. The mixture was cooled to 10-15° C. and treated 1N HCl (245 mL). The organic layer was separated, washed with water (245 mL) and brine (245 mL) to give a solution of A-4 that can be used directly in the next step without further purification.

To a stirred solution of A-4 in MTBE (~375 mL, ~108 mmol, 1 eq.) under N$_2$ was added NaHCO$_3$ (34.1 g, 406 mmol.~3.7 eq.) and (Boc)$_2$O (35.5 g, 162.6 mmol, ~1.5 eq.). The mixture was heated at 50° C. for ~7 h and monitored by TLC (PE:EtOAc=2:1). After complete conversion was observed, the reaction was cooled to 15° C. and water (450 mL) was added at a rate to maintain the temperature below 20° C. and stirred. The organic layer was separated and washed with brine (2×150 mL). The organic layer was concentrated under reduced pressure (bath temperature maintained below 30° C.) to ~150 mL. Heptane (150 mL) was added. The mixture was concentrated under reduced pressure (bath temperature maintained below 30° C.) to ~150 mL. The mixture was stirred at 15° C. for 1 h and filtered. The solid was washed with heptane (30 mL) and dried under vacuum to give A-5 (60 g; ~32.1% A-5; ~67.9% Ph$_3$PO) as a solid mixture containing Ph$_3$PO that can be combined directly with A-10 in the next step.

A mixture of tosyl chloride (25.0 g, 131 mmol, 1.0 eq.) and DMF (20.1 g, 275 mmol, 2.1 eq.) was stirred under N$_2$ at 130° C. for 20 h. The reaction was cooled to 10-15° C. and water (62 mL) was slowly added so as to maintain the temperature below 30° C. The mixture was filtered, and the separated solid was washed with water (13 mL). The combined filtrates containing A-8 were added slowly to a mixture of KPF$_6$ (24.1 g, 131 mmol, 1 eq.) in water (100 mL) that had been stirred under N$_2$ at 65° C. for 1 h. The mixture was stirred at 65° C. for 1 h, and then cooled to 5° C. and stirred for 5 h. The thick slurry was vacuum-filtered, washed with cold water (50 mL). The solid (A-9) was dried under vacuum at 45-50° C. A solution of THF (100 mL) and t-BuOK (7.7 g, 68.7 mmol, 2.5 eq.) was stirred under N$_2$ for 30 mins at RT and A-9 (20.3 g, 82.5 mmol, 3 eq.) was added. The reaction was heated to 60° C. and stirred for 4 h, cooled to RT and filtered under N$_2$ through a pad of celite. The filter cake was washed with THF (20 mL), and the combined filtrates containing A-10 were combined with A-5 (31.1 g of mixture, 27.4 mmol, 1 eq.) and stirred under N$_2$ for 3 h. The mixture was cooled to 10° C. and treated dropwise with 2N HCl (~10-40 mL) to pH 3-4 at such a rate as to maintain the reaction temperature below 15° C. The pH 3-4 mixture was stirred at 10-15° C. for 2 h, filtered, cooled and washed with acetone (10 mL). The isolated solid was mixed with acetone:water (7:3, 40 mL) at RT for 3 h, filtered, and washed with acetone:water (7:3, 20 mL) to give A-6 (4.5 g, 60%) as a white solid. LCMS (ESI) m/z=275.2 [M+H]$^+$ (calc.=274.1). Retention Time=1.097 mins.

To a mixture of A-6 (18 g, 65.6 mmol, 1 eq.) under N$_2$ in MTBE (180 mL) at RT was added N,O-Bis(trimethylsilyl)acetamide (BSA, 16.0 g, 78.7 mmol, 1.2 eq.). The reaction was stirred for 30 mins and 2-trimethylsilylethyoxymethyl chloride (SEMCl, 15.3 g, 93 mmol, 1.4 eq.) was added. After addition, the mixture was stirred at RT for 4 h. The solution was then cooled to 15° C., and quenched with sat. aq. NaHCO$_3$ to pH ~4. The organic layer containing A-7 was separated and treated directly with aq. NaOH (5.25 g, 2 eq., ~1M). After addition, the mixture was stirred for 2 h at RT. The organic layer was separated, and the remaining aqueous solution was treated with 2N HCl to pH ~2-3. A white solid precipitated, which was filtered and washed with water (36 mL). The wet cake was slurried in water (180 mL), stirred for 5 h, and filtered. The isolated solid was washed with water (2×36 mL) and dried under vacuum to give compound (A) (22.9 g, 92.7%) with 99.1% purity. ¹H NMR (400 MHz, DMSO-d 6): δ 8.88 (s, 1 H), 7.49-7.41 (m, 5 H), 5.57 (s, 2 H), 522 (s, 2 H), 3.63 (t, J=8 Hz, 2H), 0.87 (t, J=8 Hz, 2H), 0.02 (S, 9 H).

Example 3—Compound (B)

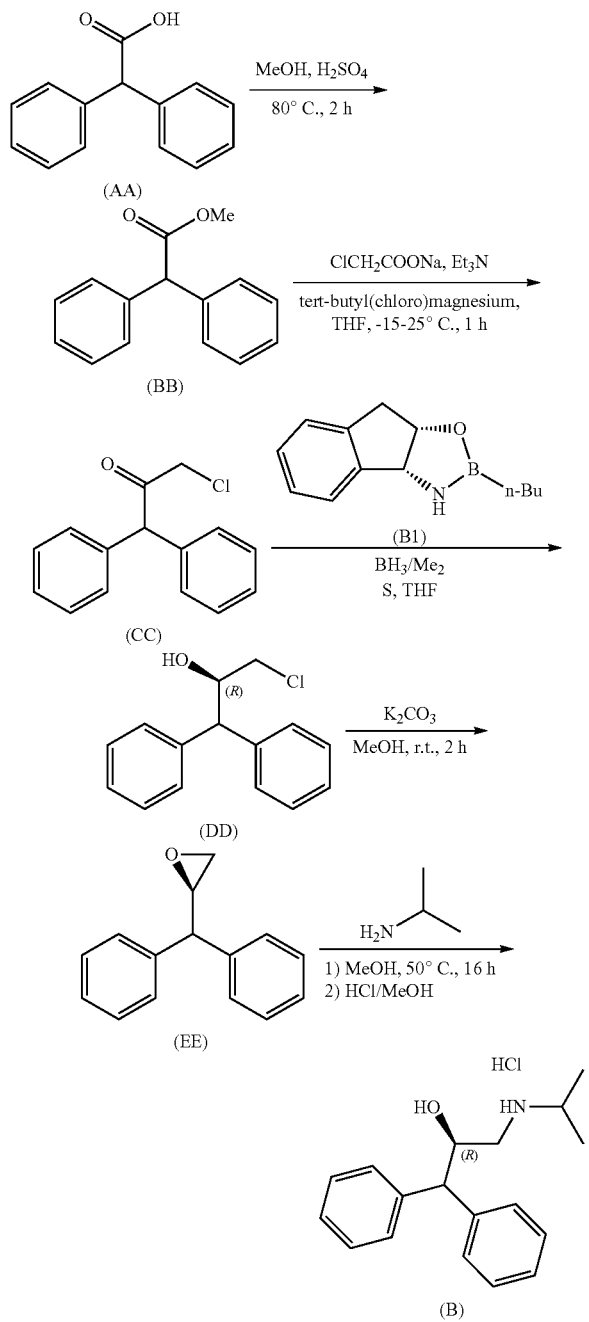

A mixture of compound (AA) (280.00 g, 1.32 mol, 1.00 eq.) was dissolved in MeOH (1.4 L), and then H₂SO₄ (140.00 mL) was added. The mixture was stirred at 80° C. for 2 h and monitored by TLC (PE:EA=5:1), which showed no starting material after 2 h. The mixture was concentrated. The residue was washed with aq. NaHCO₃ (2000 mL) and extracted with EA (1000 mL). The organic layer was concentrated to give compound (BB) (280 g, 84.37%). ¹H NMR: (CDCl₃, 400 MHz): δ7.38-7.29 (m, 10H), 5.07 (s, 1H), 3.78 (s, 3H).

To a solution of compound (BB) (150.00 g, 662.92 mmol, 1.00 eq.) were dissolved Et₃N (201.24 g, 1.99 mol, 3.00 eq.) and ClCH₂COONa (231.65 g, 1.99 mol, 3.00 eq.) in THF (750.00 mL). Tert-butyl(chloro)magnesium (1.7 M, 1.56 L, 4.00 eq.) was added at −15° C. for 1 h. The mixture was stirred at 25° C. for 1 h and monitored by TLC (PE:EA=10:1), which showed no starting material after 1 h. The reaction was quenched using 1 N HCl (3 L) and extracted with EA (1500 mL×3). The organic layer was concentrated, and the residue was washed with MTBE (200 mL). The residue was dried to give compound (CC) (120.00 g, 66.57%) as an orange solid. ¹H NMR: (CDCl₃, 400 MHz): δ7.37-7.24 (m, 10H), 5.43 (s, 1H), 4.20 (s, 2H).

A solution of BH₃-Me₂S (8.17 mL, 1.00 eq.) and (B1) (8.17 mL, 8.17 mmol, 0.1 eq.) were dissolved in THF (120 mL). The mixture was stirred at 25° C. for 1 h. Compound (CC) (20.00 g, 81.7 mmol, 1.00 eq.) in THF (200 mL) was added at 40° C. for 2 h. To the mixture was added MeOH (20 mL) and 1 N HCl (20 mL). The mixture was stirred for 30 mins, and then extracted with EA (300 mL×3). The organic layer was concentrated, and the residue was purified by column chromatography (SiO₂, PE to PE:EA=20:1) to give compound (DD) (14.00 g, 63.87%, 90.3% ee, 93% HPLC purity) as a colorless oil.

To a solution of compound (DD) (22.00 g, 89.17 mmol, 1.00 eq.) dissolved in MeOH (220 mL) was added K₂CO₃ (36.97 g, 267.51 mmol, 3.00 eq.). The mixture was stirred at 25° C. for 2 h and monitored by TLC (PE:EA=10:1), which showed no starting material after 2 h. The mixture was filtered, and water (500 mL) was added to the filtrate. The filtrate was then extracted with PE (200 mL×3). The organic layer was concentrated to give compound (EE) (16.00 g, 76.80%, 83.3% ee) as a colorless oil. ¹H NMR: (CDCl₃, 400 MHz): δ7.40-7.27 (m, 10H), 3.89 (d, J=7.2 Hz, 1H), 3.57-3.54 (m, 1H), 2.89-2.87 (m, 1H), 2.56-2.54 (m, 1H).

To a solution of compound (EE) (16.00 g, 76.09 mmol, 1.00 eq.) dissolved in MeOH (160 mL) was added propan-2-amine (89.96 g, 1.52 mol, 20.00 eq.). The mixture was stirred at 50° C. for 16 h and monitored by TLC (PE:EA=10:1), which showed no starting material after 16 h. The mixture was concentrated, and the residue was dissolved in MeOH (30 mL). 4 N HCl/MeOH (100 mL) was added, and the mixture was stirred at 25° C. for 30 mins. The mixture was directly concentrated under reduce pressure at 40° C. The residue was rinsed with TBME (100 mL×2) to give a white solid (22 g, 90.7% ee). This white solid was re-crystallization using MeOH (60 g) and isopropanol (138.6 g) to give compound (B) (14.00 g, 60.10%, 99.4% ee, 99.9% HPLC purity) as a white solid. ¹H NMR: (DMSO, 400 MHz): δ9.08 (s, 1 H), 8.69 (s, 1H), 7.40-7.19 (m, 10H), 5.63 (d, J=6 Hz, 1H), 4.72 (s, 1H), 4.043 (d, J=3.6 Hz, 1H), 3.28-3.25 (m, 1H), 2.74 (s, 1H), 1.17 (dd, J₁=23.6 Hz, J₂=6.8 Hz, 6H).

Example 3A

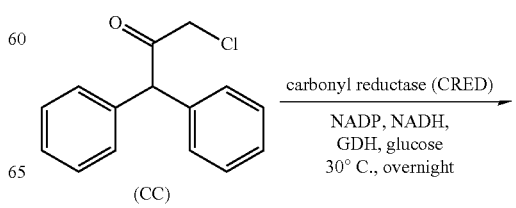

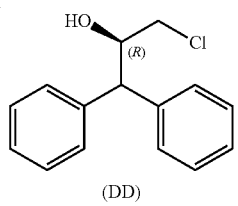

(DD)

To a 1.5 mL Eppendorf tube/96 well plate containing enzyme (5-10 mg) was added a stock solution containing NADP (1.0 mg), NADH (1.0 mg), GDH (glucose dehydrogenase) (2.0 mg) and glucose (30 mg) in pH 7 KH$_2$PO$_4$ buffer solution (1 mL). To this mixture was added a solution of chloroketone 1 (5.0 mg) in DMSO (50 μL). The resulting reaction mixture was shaken at 30° C. and 220 rpm overnight. To analyse, the reactions were quenched with acetonitrile (500 μL), shaken for 10 mins and centrifuged at 13000 rpm for 2 mins, then the supernatant was pipetted into clean HPLC vials and injected directly on reverse phase HPLC.

Of the 280 CREDs (carbony reductases) screened, all have been analysed by TLC. Eleven enzymes showed evidence of alcohol formation by TLC analysis. Subsequent chiral HPLC analysis determined if any had the required (R)-selectivity. Of these eleven hit enzymes, CRED-41, CRED-52 and CRED-121 favoured the formation of desired (R)-alcohol (DD) with high enantiomeric excess. Enzymes demonstrating activity for product formation and their conversion by HPLC peak area are shown in Table 1 below.

TABLE 1

Summary of CRED screening results with stock enzymes

| Almac Enzyme | Conversion (%)$^a$ | Chloroketone (%) | (S)-alcohol (%) | (R)-alcohol (%) |
|---|---|---|---|---|
| CRED-41 | 99.5 | 0.5 | 0.0 | 99.5 |
| CRED-52 | 44.21 | 55.79 | 0.0 | 44.21 |
| CRED-155 | 13.44 | 86.56 | 1.35 | 12.09 |
| CRED-163 | 13.0 | 87.0 | 0.0 | 13.0 |
| CRED-121 | 86.46 | 13.56 | 0.0 | 86.46 |

Example 3B

Synthesis of (R)-Alcohol (Compound DD) with CRED-121:

A three neck 1 L RBF (round bottom flask) was fitted with a mechanical stirrer and placed in a preheated oil-bath at 30° C. To this RBF was added pH 7.5 KH$_2$PO$_4$ buffer solution (300 mL) containing CRED-121 (900 mg), NADP (7.5 mg, 0.25 wt %) and GDH (30 mg, 1 wt %). The resulting reaction mixture was stirred at 30° C. for 10 min and then a solution of chloroketone (3.0 g) in MTBE (60 mL) was added. The reaction mixture was stirred at 30° C. for 20 h. A sample of reaction mixture (0.5 mL) was quenched with acetonitrile (5.0 mL) and analysed by chiral HPLC. An additional amount of CRED-121 CFE (cell free extract) (210 mg), NADP (67.5 mg) and GDH (30 mg) were added to the reaction mixture and stirred for an additional 72 h at 30° C. HPLC analysis showed the desired (R)-alcohol (compound DD) with >74% HPLC peak area. CRED-121 CFE (1 g) was added along with GDH (30 mg), NADP (75 mg) and stirred for 4 h. The reaction had achieved >98% HPLC peak area for (R)-alcohol (compound DD) at this point. After completion of the reaction, the reaction mixture was transferred into a one litre separating funnel and the organic layer separated from aqueous mixture. The aqueous layer was extracted with MTBE (4×60 mL) and the combined organic layers were centrifuged to break the emulsion. The organic layer from the centrifuged reaction mixture and was dried with MgSO$_4$. The volume of organic layer was reduced to 30 mL.

Example 4—Compound (I)

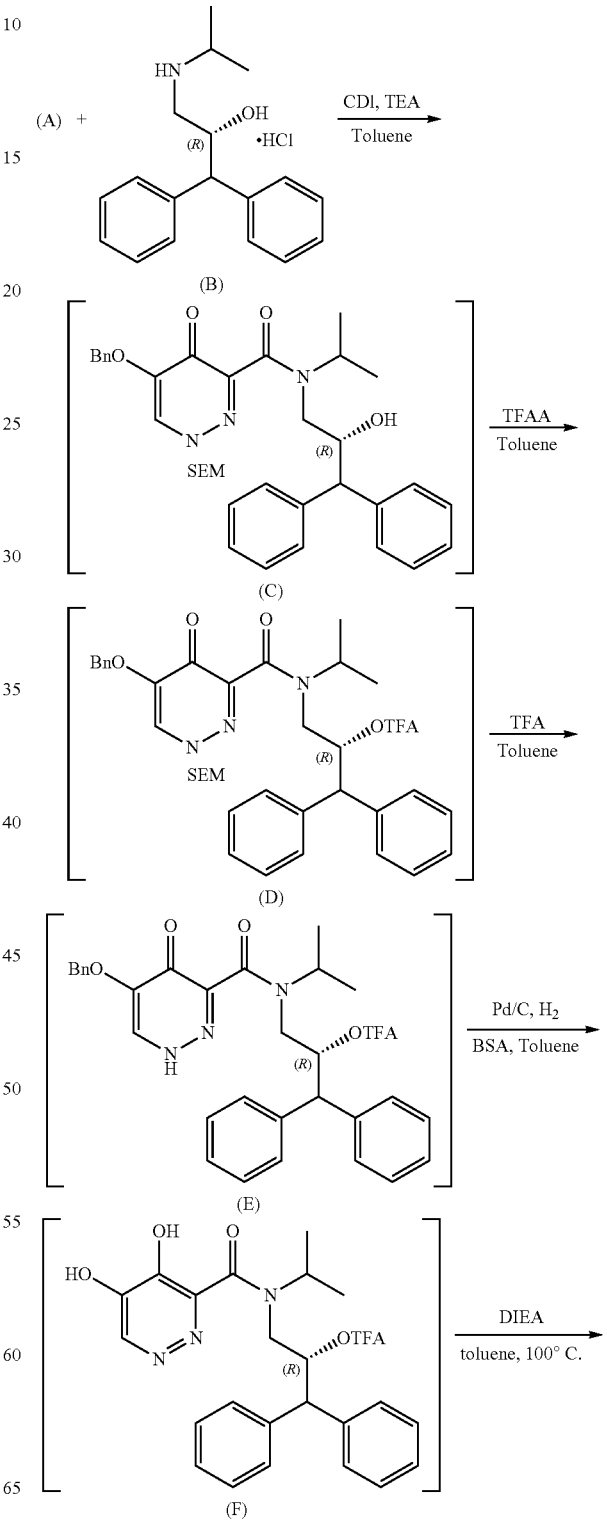

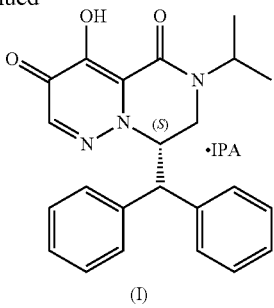

(I)

A mixture of compound (A) (7.5 Kg, 1.3 eq.) and CDI (0.71 Kg, 1.35 eq.) in toluene (61 Kg) was stirred at 25° C. for 2 h under N₂. TEA (4.65 Kg, 3.0 eq.) and compound (B) (4.7 Kg, 1.0 eq.) were added. The mixture was stirred at 50-60° C. for 4 h. The mixture was then cooled to 15-25° C., washed with 5% NaOH (62 Kg), 2N HCl (40 Kg) and 7% NaHCO₃ (40 Kg) successively. The organic layer was concentrated at below 55° C. to give crude compound (C) (~25 L volume).

TFAA (4.0 Kg, 1.24 eq.) was added to compound (C) obtained from the previous step, and the mixture was stirred at 25-30° C. for 3 h. TFA (14.8 Kg) was added, and the mixture was stirred at 25-30° C. for 10 h. The mixture was concentrated at below 35° C. to ~25 L in volume. Toluene (41 Kg) was added. The mixture was washed with water (113 Kg), and pH 7 Na₂HPO₄/NaH₂PO₄.H₂O buffer (42 Kg×3). The organic layer was washed with water (38 Kg) and 25% brine (42 Kg), dried with Na₂SO₄ (45 Kg) and filtered. The filtered solution containing compound (E) was used in the next step.

To a solution of compound (E) from the previous step was added BSA (6.3 Kg, 2.0 eq.) and Pd/C (0.5 Kg). The mixture was hydrogenated at 25-30° C. under 0.28-0.34 MPa of pressure for 4 h. The mixture was filtered through Celite and was used in the next step.

A solution of compound (F) was heated to 100-110° C. and DIPEA (6.1 Kg, 3.0 eq.) was added. The mixture was stirred for 2 h, and then filtered through Celite. The filtrate was concentrated at below 55° C. to ~12 L in volume. To this solution was added IPA (27 Kg), and the mixture was stirred at 45-55° C. The mixture was then slowly cooled to 3-7° C. to induce crystallization of compound (I). The mixture was filtered to give the product (2.2 Kg), which was dried under N₂ to give compound (I) as a IPA solvate (2.14 Kg, 98.7% purity, 36% yield over 5 steps).

Example 5—Compound (II)

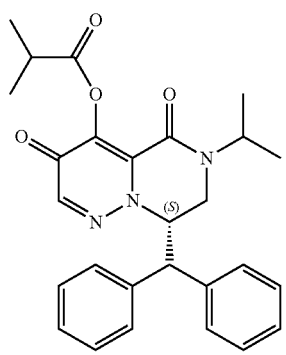

To a solution of compound (I) (2.1 Kg, 1.0 eq.) in ethyl acetate (19 Kg) was added DIPEA (1.32 Kg, 1.8 eq.) and isobutyryl chloride (0.8 Kg, 1.4 eq.) sequentially at 20-25° C. The mixture was stirred for 2 h. MeOH (0.17 Kg) was added, and the mixture was stirred for 2 h. The mixture was then washed with water (46 Kg) and pH 7 Na₂HPO₄/NaH₂PO₄.H₂O buffer (2×23 Kg). The organic layer was washed with water (21 Kg), dried with Na₂SO₄ (12 Kg) and filtered. The filtered solution was concentrated to ~15 L. To this solution was added n-heptane (16 Kg) over 2-3 h. The mixture was then cooled to 0-5° C. in 1-2 h. The solid was collected and dried to give compound (II) (2.00 Kg, 81%).

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of preparing a compound of Formula (DD)

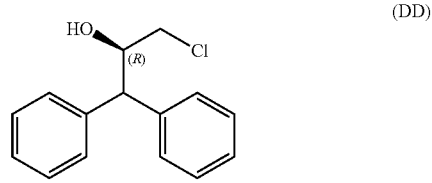

comprising the step of reacting a compound of Formula (CC)

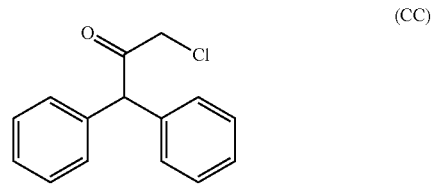 [SMILES: O=C(CCl)C(c1ccccc1)c1ccccc1]

with a hydride source in the presence of a carbonyl reductase to form a compound of Formula (DD), wherein the carbonyl reductase is selected from CRED-121, CRED-41, CRED-52, CRED-155, and CRED-163.

2. The method of claim 1, wherein the carbonyl reductase is selected from CRED-121 and CRED-41.

3. The method of claim 2, wherein the carbonyl reductase is CRED-121.

4. The method of claim 2, wherein the carbonyl reductase is CRED-41.

5. The method of claim 1, wherein the hydride source is (i) a cofactor selected from NAD and NADP, (ii) a reducing sugar, and (iii) a dehydrogenase that dehydrogenates the reducing sugar.

6. The method of claim 5, wherein the reducing sugar is glucose and the dehydrogenase is glucose dehydrogenase.

7. The method of claim 5, wherein the cofactor is NADP.

8. The method of claim 5, wherein the cofactor is NAD.

* * * * *